(12) United States Patent
Steinhardt et al.

(10) Patent No.: US 7,238,202 B2
(45) Date of Patent: Jul. 3, 2007

(54) OSSICULAR REPLACEMENT PROSTHESIS

(75) Inventors: Uwe Steinhardt, Hirrlingen (DE); Daniel F. aWengen, Binningen (CH)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 0 days.

(21) Appl. No.: 10/982,961

(22) Filed: Nov. 4, 2004

(65) Prior Publication Data
US 2005/0165481 A1   Jul. 28, 2005

(30) Foreign Application Priority Data
Jan. 23, 2004   (DE)   .................. 20 2004 001 008 U

(51) Int. Cl.
*A61F 2/18*   (2006.01)
(52) U.S. Cl. ....................................... 623/10
(58) Field of Classification Search ................. 623/10, 623/11.11; 600/25; 607/55, 137
See application file for complete search history.

(56) References Cited
U.S. PATENT DOCUMENTS

| | | | |
|---|---|---|---|
| 3,473,170 A | * | 10/1969 | Haase et al. .................. 623/10 |
| 3,711,869 A | | 1/1973 | Shea, Jr. |
| 4,655,776 A | * | 4/1987 | Lesinski ....................... 623/10 |
| 6,203,571 B1 | | 3/2001 | Magnan et al. |
| 2002/0045939 A1 | | 4/2002 | Kurz |
| 2003/0130734 A1 | | 7/2003 | Antonelli et al. |
| 2004/0064183 A1 | | 4/2004 | Wengen et al. |
| 2005/0027357 A1 | | 2/2005 | Steinhardt et al. |

FOREIGN PATENT DOCUMENTS

| | | |
|---|---|---|
| DE | 200 14 659 U1 | 1/2001 |
| DE | 202 12 771 U1 | 12/2002 |
| DE | 203 10 609 U1 | 10/2003 |
| FR | 2 769 492 | 4/1999 |

* cited by examiner

*Primary Examiner*—David J. Isabella
(74) *Attorney, Agent, or Firm*—Michael J. Striker

(57) ABSTRACT

An auditory ossicle prosthesis (10) which is fastened to the limb of incus (20) of the human ossicular chain and to the stapes, or is inserted directly into the inner ear, whereby the auditory ossicle prosthesis (10) is made of an elastic material or a material having at least one hinged connection, and whereby the auditory ossicle prosthesis (10), starting at its articulation on the limb of incus (20), largely traces the course of the natural limb of incus (20) to its end or past it, and, angled downward in the region of the level of the natural end of the limb of incus (20), extends to the other endpoint of the auditory ossicle prosthesis (10) on the stapes or at/in the inner ear.

10 Claims, 3 Drawing Sheets

OSSICULAR REPLACEMENT PROSTHESIS

The present invention concerns an ossicular replacement prosthesis which is fastened at one end to the limb of incus of the human ossicular chain and to the stapes at the other end, or it is inserted directly into the inner ear.

Ossicular replacement prostheses are used to conduct sound from the ear drum to the inner ear in patients in whom the auditory ossicles of the human middle ear are partially or completely missing or damaged. The ossicular replacement prosthesis has two ends. Depending on the actual circumstances, one end of the ossicular replacement prosthesis is fastened to the limb of incus of the human ossicular chain, for example, and the other end of the ossicular replacement prosthesis is fastened to the stapes of the human ossicular chain, for example, or it is inserted directly into the inner ear.

Since the anatomical conditions of the ear, such as the position, shape and size of the stapes, the incus, the hammer and the ear drum vary, it is advantageous when ossicular replacement prostheses are not rigid in design, but instead have a certain amount of flexibility or variability. Various fastening and coupling devices for auditory ossicles which have elastic parts and/or joints to achieve this flexibility/variability are known. Sound transmission between the ear drum and the inner ear is often enabled to a limited extent with the known ossicular replacement prostheses, because they are not able to fully replace the natural anatomical configurations of the ossicular chain.

The object of the present invention, therefore, is to create an ossicular replacement prosthesis which enables improved sound transmission between the limb of incus and the inner ear.

According to the present invention, this object is attained using an ossicular replacement prosthesis which is fastened at one end to the limb of incus of the human ossicular chain, for example, and is fastened to the stapes at the other end, or it is inserted directly into the inner ear, whereby the ossicular replacement prosthesis is made of an elastic material or a material which includes at least one hinge, and whereby the ossicular replacement prosthesis, starting at its articulation on the limb of incus, largely traces the course of the natural limb of incus to its end or past it, and, angled downward in the region of the level of the natural end of the limb of incus, extends to the other endpoint of the auditory ossicle prosthesis on the stapes or at/in the inner ear.

The ossicular replacement prosthesis according to the present invention therefore has the substantial advantage that the transition from the limb of incus to the stapes replicates the anatomical conditions of the natural ossicular chain to the greatest extent possible. The prosthesis according to the present invention is connected to the limb of incus approximately 1 mm behind the distal end of the limb; via the orientation of the prosthesis in the direction of the extension of the natural limb, lever ratios can be obtained and/or simulated which correspond to the natural circumstances to the greatest extent possible. The extension of the prosthesis according to the present invention is angled downward hingedly and/or elastically so that sound transmission can take place such that it is adapted to the spacial conditions in the middle ear, as it does with the natural ossicular chain. Compared with the prostheses known from the related art, the lever ratios with the prosthesis according to the present invention are greatly improved, so that substantially improved listening comfort is achieved with the new prosthesis.

The prosthesis according to the present invention can be made of tissue-compatible and bone-compatible plastics, composite fiber materials or metals which support and/or ensure the mobility of the angled course of the prosthesis according to the present invention.

In a preferred embodiment of the present invention, the prosthesis is fastened to the limb of incus using a first clip, on which a first bar is formed, the bar terminating in an end configured as a ball which is supported in a U-shaped socket part which transitions into a second bar that terminates as a cylinder or in a second clip.

With this object-based embodiment of the ossicular replacement prosthesis according to the present invention, a high degree of mobility is achieved, which provides improved support for sound transmission in the middle ear. The ball joint permits a very high degree of mobility of the prosthesis according to the present invention to be achieved and, in fact, along a course that replicates that of the human ossicular chain.

If the prosthesis according to the present invention is fastened using clips and/or a cylinder on the limb of incus and/or on the stapes, or if it is inserted directly into the inner ear using a cylinder, the flexibility or mobility of the prosthesis according to the present invention is not hindered.

A particularly preferred embodiment of a hinge in the angled region of the prosthesis is formed using a cylinder and a U-shaped socket part in which the ball is supported in openings in the side walls of the socket part. Using a structural embodiment of this nature, the ball in the U-shaped socket part can move without restriction in every direction and ensure the best possible sound transmission.

In a further embodiment of the present invention, the first and/or second clip is formed of two flexible tongues arranged in a V or U-shape. An embodiment of this type improves the hold of a clip. If the contact points of the clips are also roughened at the points where they bear against the limb of incus and/or the stapes, then a secure, long-lasting fastening of the ossicular replacement prosthesis according to the present invention is ensured.

The ossicular replacement prosthesis according to the present invention can be configured on one end as a cylinder, which is inserted directly into the inner ear. A second clip is not necessary with this embodiment.

A handle is formed on the first and/or second clip to simplify placement of the ossicular replacement prosthesis according to the present invention. This configuration makes it easier to place the prosthesis according to the present invention in the middle ear.

The ossicular replacement prosthesis itself according to the present invention is made of a biocompatible material and/or a composite material which can contain plastic parts and/or metallic components such as titanium, titanium alloys or nitinol. The prosthesis itself can be made entirely of one of the metals named.

An embodiment of the ossicular replacement prosthesis according to the present invention is shown in the drawing, below. The embodiments shown in the drawing are to be understood as examples and do not depict the object according to the invention to scale.

Figure 1:
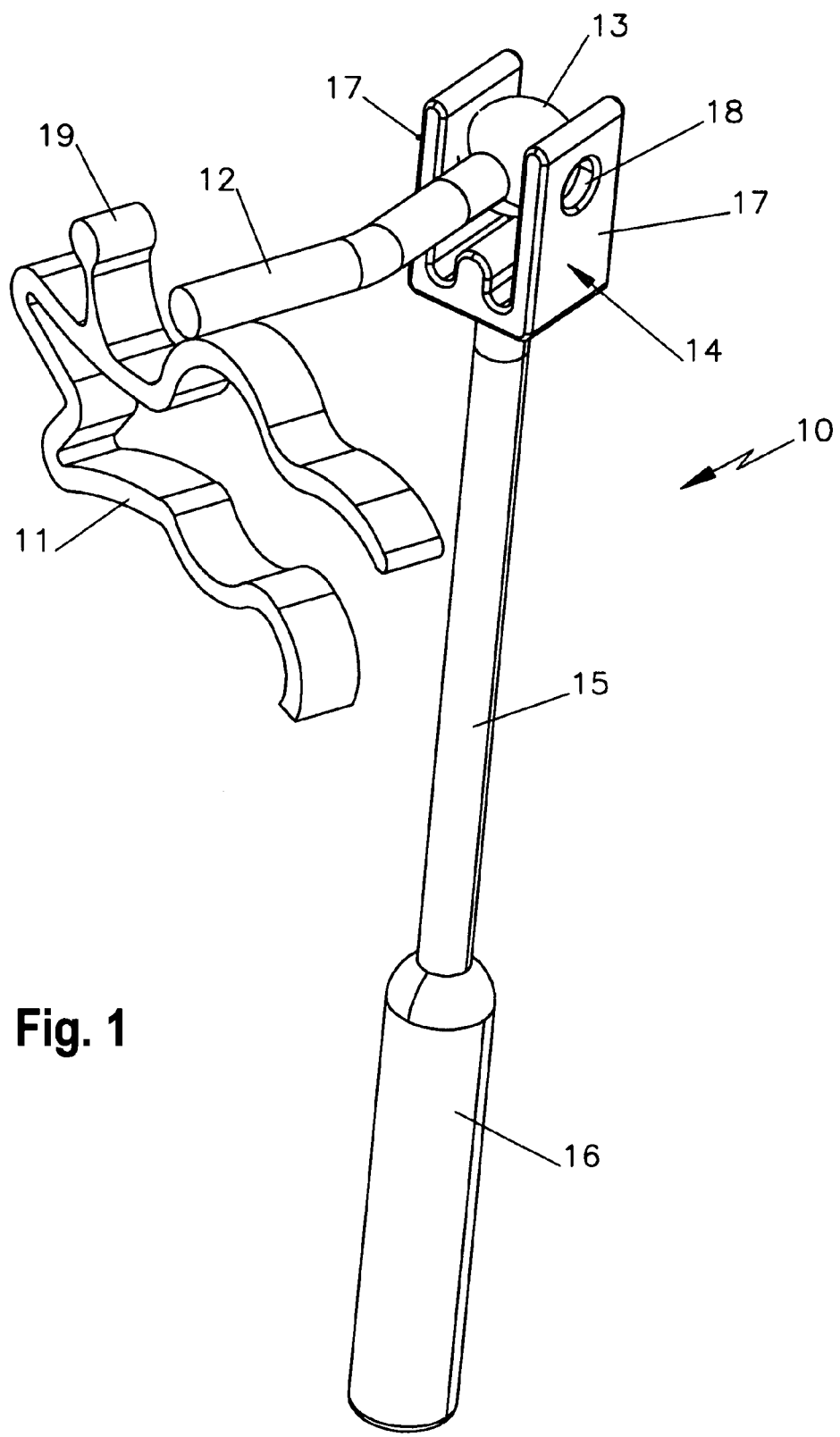
FIG. 1 shows an ossicular replacement prosthesis according to the present invention in a spacial representation with an angled section which is designed as a joint.

FIG. 1 shows a perspective illustration of an ossicular replacement prosthesis 10 according to the present invention which has a first clip 11 to which a first bar 12 is fastened. First bar 12 extends in a slightly angled manner; it need not extend in a straight line. Bar 12 is bonded with first clip 11, which is configured as a V-shaped clip with a high degree of flexibility. First clip 11 and first bar 12 can be made of a titanium alloy.

First bar 12 terminates—diametrically opposed to first clip 11—in a ball 13 which is supported in a U-shaped socket part 14. A second bar 15 abuts U-shaped socket part 14, the bar transitioning into a cylinder 16. Instead of cylinder 16, a second clip can be formed on second bar 15. Ossicular replacement prosthesis 10 according to the present invention is held in the middle ear on the limb of incus at one end and on the stapes and/or in the inner ear at the other end via first clip 11 and/or cylinder 16 or the second clip formed as an alternative on the end of second bar 15.

U-shaped socket part 14 includes side walls 17, in each of which openings 18 are formed. Ball 13 is held in a hingedly supported manner in these openings 18, so that a high degree of mobility of ossicular replacement prosthesis 10 between first clip 11 and cylinder 16 is given. A handle 19 is formed on first clip 11, which simplifies placement of first clip 11 on the limb of incus.

Figure 2:
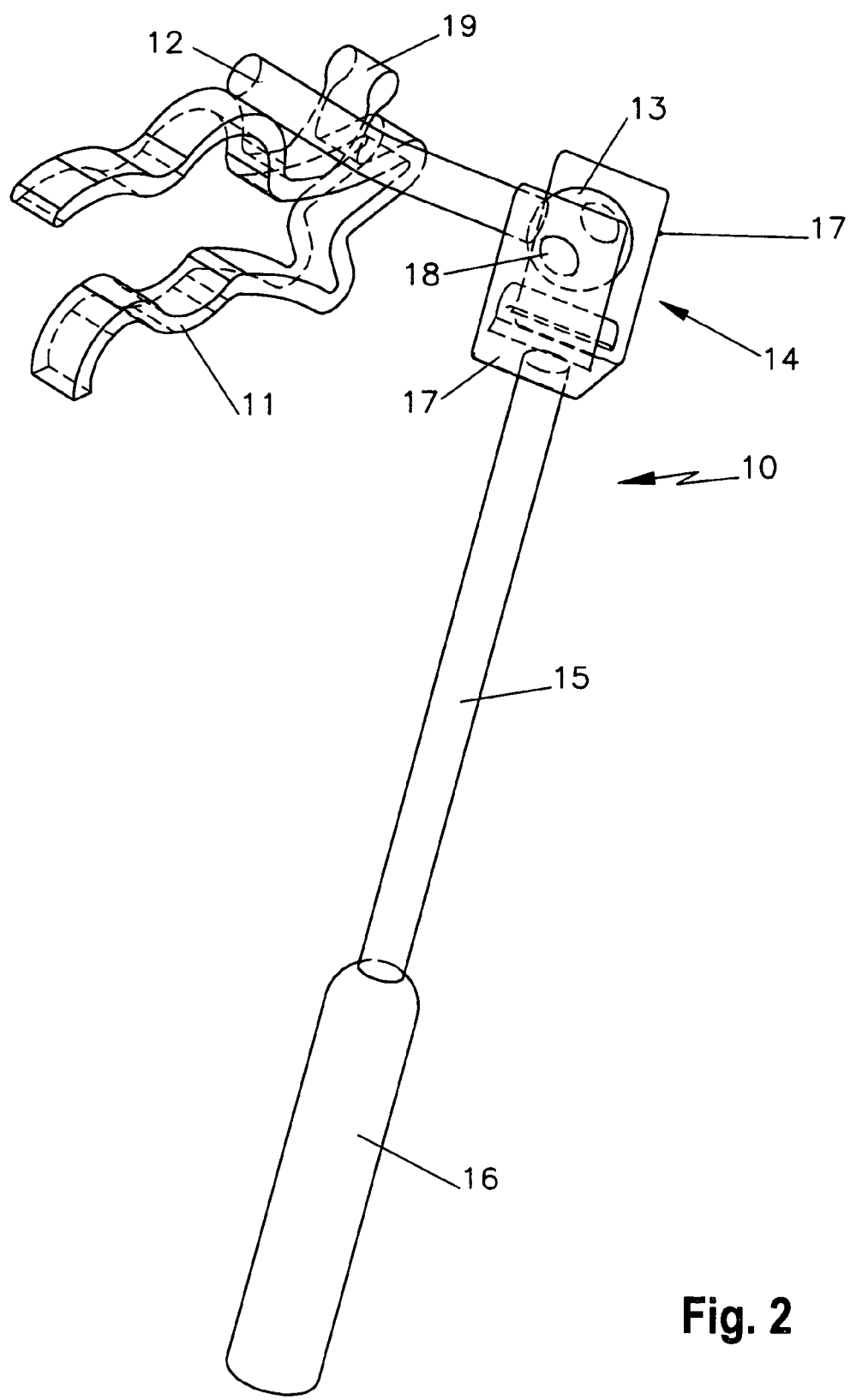
FIG. 2 shows an ossicular replacement prosthesis according to FIG. 1 from a different viewpoint.

FIG. 2 shows ossicular replacement prosthesis 10 according to the present invention from FIG. 1 in a further perspective illustration from a different viewpoint, whereby the same object features are labelled with the same reference numerals. The coupling of first bar 12 to second bar 15 via U-shaped socket part 14 is clearly shown, and the high degree of mobility of ball 13, supported in openings 18 of side walls 17 of U-shaped socket part 14 is also clearly shown. If ossicular replacement prosthesis 10 according to the present invention is placed in the middle ear, the ball joint results in a high degree of mobility between first clip 11 and cylinder 16.

Figure 3:
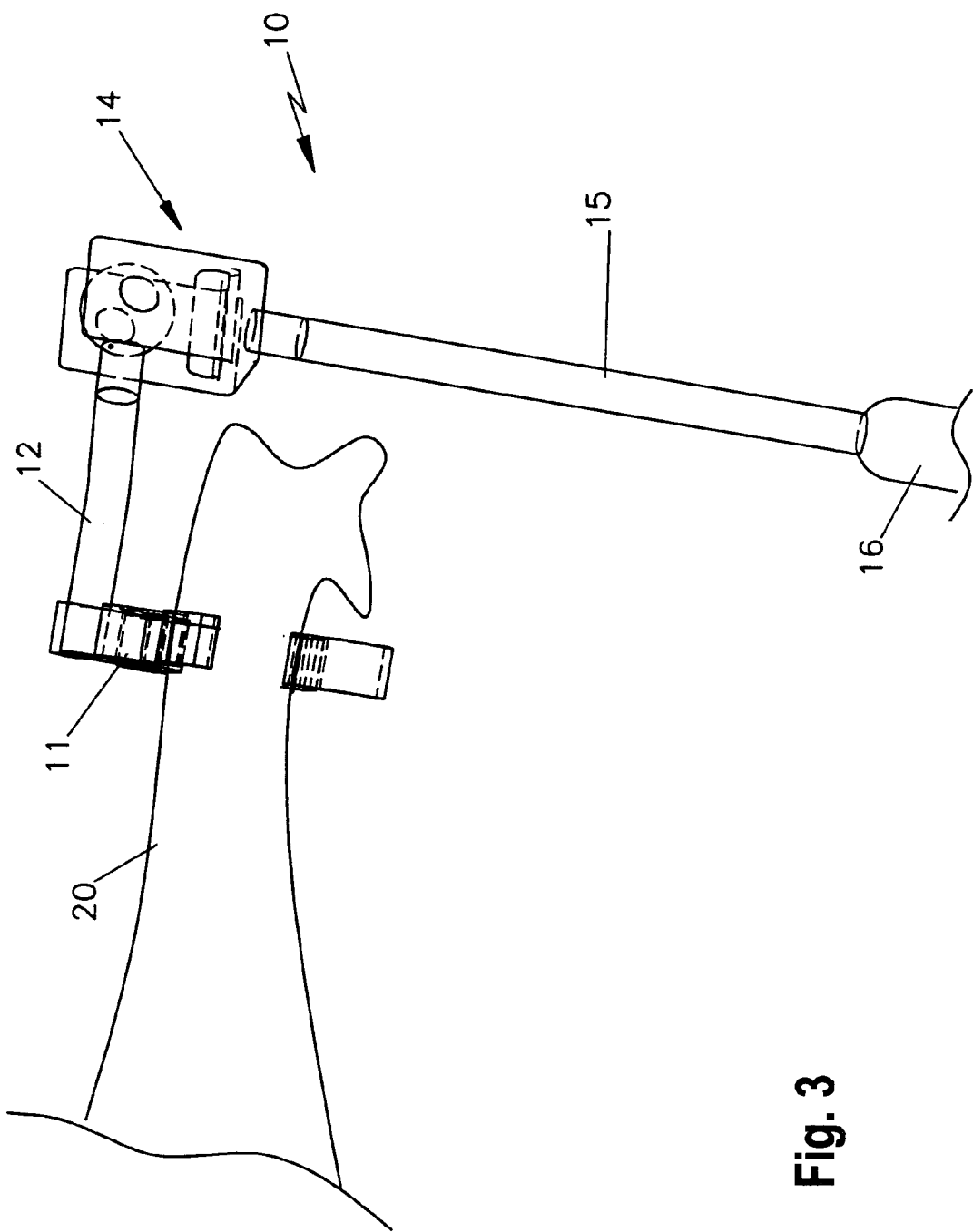
FIG. 3 shows a section of an ossicular replacement prosthesis according to the present invention, according to FIGS. 1 and 2, as it is articulated and/or fastened to the limb of incus.

FIG. 3 shows a section of a limb of incus 20 and ossicular replacement prosthesis 10 shown in FIGS. 1 and 2, as it is fastened to limb of incus 20 using first clip 11. Ossicular replacement prosthesis 10 extends past the natural limb of incus 20 by the fact that first bar 12 transitions, hingedly connected, into second bar 15, which terminates in cylinder 16, part of which is shown.

With ossicular replacement prosthesis 10 shown in FIGS. 1 through 3, a prosthesis is shown that allows the lever ratiosand/or the tuning of the middle ear for sound transmission to be considerably improved.

What is claimed is:

1. An auditory ossicle prosthesis (10) which is configured to be fastened to the limb of incus (20) of the human ossicular chain and to be inserted directly into the inner ear, whereby the auditory ossicle prosthesis (10) having at least one hinged connection, and whereby the auditory ossicle prosthesis (10) includes a first clip extending in a first direction that is configured to be fastened to the limb of incus (20), a first bar (12) is formed on the clip and extends transversely to the first direction starting at its articulation on the limb of incus (20) and traces the course of the natural limb of incus (20) to its end or past it; the first bar terminating in an articulated joint that transitions into a second bar (15), the second bar being angled downward in the region of the level of the natural end of the limb of incus (20) to extend to the other endpoint of the auditory ossicle prosthesis (10) or at/in the inner ear, which extends back substantially in the first direction and terminates as a cylinder (16) so that the first clip and the second bar extend transversely to and from the first bar.

2. The auditory ossicle prosthesis as recited in claim 1 wherein the first bar (12) terminates in an end configured as a ball (13) which is supported in a U-shaped socket part (14) that transitions into the second bar (15).

3. The auditory ossicle prosthesis as recited in claim 2, wherein the U-shaped socket part (14) includes openings (18) in side walls (17) in which the ball (13) is supported.

4. The auditory ossicle prosthesis as recited in claim 2 wherein the first clip (11) is formed of two flexible tongues arranged in a V or U-shape.

5. The auditory ossicle prosthesis as recited in claim 2, wherein the first clip (11) is roughened up at its contact points with the limb of incus (20).

6. The auditory ossicle prosthesis as recited in claim 2, wherein the first clip (11) includes a handle (19).

7. The auditory ossicle prosthesis as recited in claim 1, wherein the prosthesis or parts thereof are made of titanium, a titanium alloy, biocompatible plastics or composite fiber materials, or nitinol.

8. A method for replicating the anatomical conditions of the natural human ossicular chain, comprising the steps of inserting an ossicular replacement prosthesis (10) as a transition means from the limb of incus to the stapes or directly into the inner ear; providing the ossicle prosthesis (10) having at least one hinged connection, and whereby the auditory ossicle prosthesis (10) includes a first clip extending in a first direction that is configured to be coupled to the limb of incus and fastening the clip to the limb of incus (20), a first bar (12) is formed on the clip and extends transversely to the first direction starting at its articulation on the limb of incus (20) and traces the course of the natural limb of incus (20) to its end or past it; the first bar terminating in an articulated joint that transitions into a second bar (15), the second bar being angled downward in the region of the level of the natural end of the limb of incus (20) to extend to the other endpoint of the auditory ossicle prosthesis (10) or at in the inner ear, which extends back substantially in the first direction and terminates as a cylinder (16) so that the first clip and the second bar extend transversely to and from the first bar.

9. The method as recited in claim 8, and further comprising a lever ratio of the ossicular chain via the orientation of the prosthesis in the direction of the extension of the natural limb.

10. The method as recited in claim 8, and further comprising angling an extension of the prosthesis downward hingedly and/or elastically so that sound transmission can take place such that it is adapted to the special conditions in the middle ear, as it does with the natural ossicular chain.

* * * * *